United States Patent [19]
Pfreundschuh

[11] Patent Number: 5,840,568
[45] Date of Patent: Nov. 24, 1998

[54] HODGKIN'S DISEASE ASSOCIATED MOLECULES AND USES THEREOF

[75] Inventor: Michael Pfreundschuh, Homburg/Saar, Germany

[73] Assignee: Ludwig Institute for Cancer Research, New York, N.Y.

[21] Appl. No.: 668,128

[22] Filed: Jun. 21, 1996

Related U.S. Application Data

[63] Continuation-in-part of Ser. No. 644,116, May 10, 1996, which is a continuation-in-part of Ser. No. 580,980, Jan. 3, 1996, which is a continuation-in-part of Ser. No. 479,328, Jun. 7, 1995.

[51] Int. Cl.$^6$ .............................. C12N 1/20; C12N 15/00; G01N 33/00; C07H 21/04
[52] U.S. Cl. ...................................... 435/252.3; 435/320.1; 436/94; 536/23.1; 536/23.5; 536/24.31; 935/1; 935/22; 935/66; 935/77; 935/78
[58] Field of Search ........................... 435/6, 69.1, 252.3, 435/320.1; 436/94; 536/23.1, 23.5, 24.31; 935/1, 22, 66, 77, 78

[56] References Cited

PUBLICATIONS

Bilbe et al., "Restin: a novel intermediate filament–associated protein highly expressed in the Reed–Sternberg cells of Hodgkin's disease," The Embo Journal, vol. 11, No. 6, pp. 2103–2113, Jun. 1992.

*Primary Examiner*—Bradley L. Sisson
*Attorney, Agent, or Firm*—Felfe & Lynch

[57] ABSTRACT

The invention describes identification and isolation of molecules associated specifically with Hodgkin's Disease. Uses of the molecules are described as well.

19 Claims, 4 Drawing Sheets

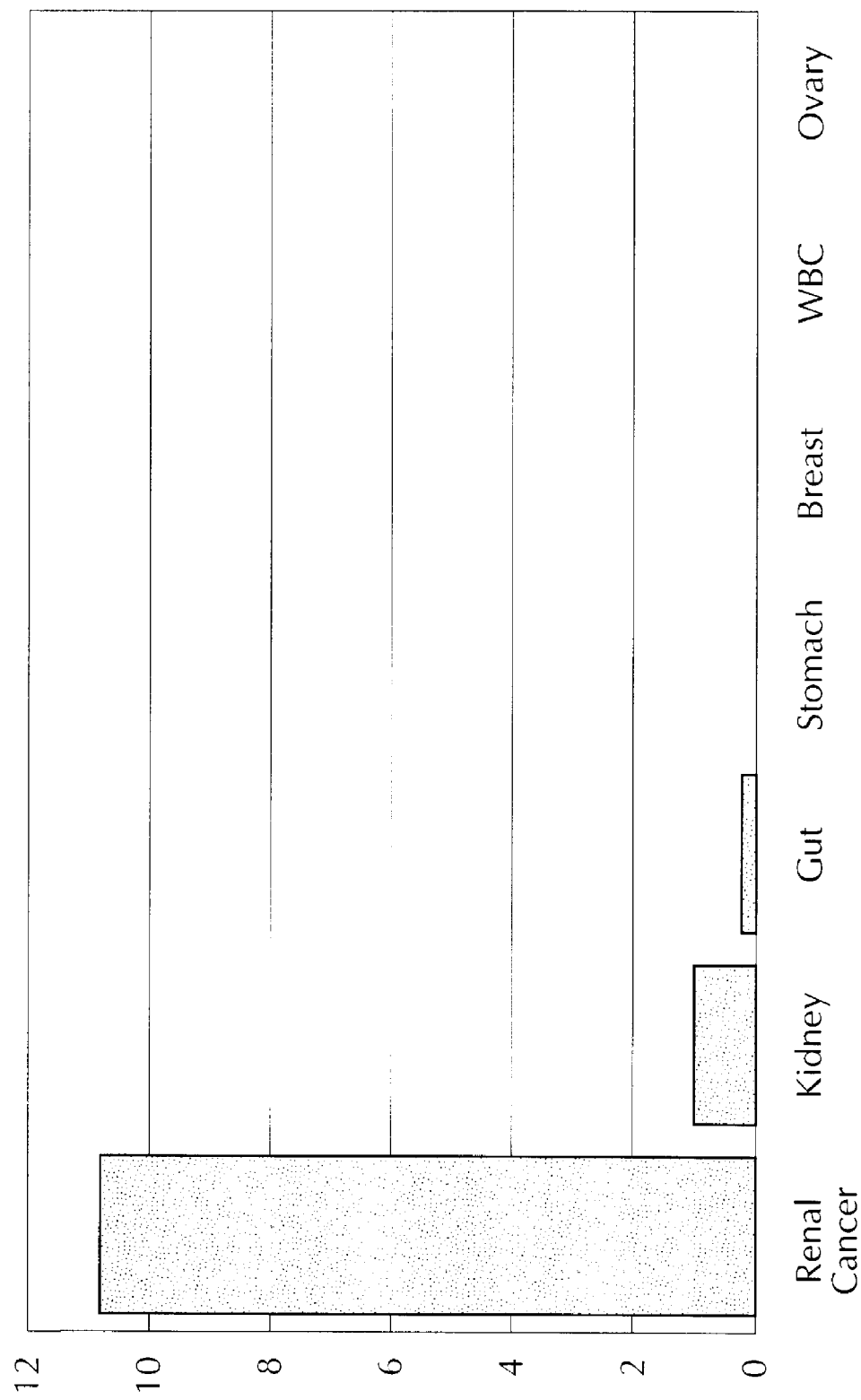

FIG. 4

```
ORIGIN
    1 ATCTGCAGAA TTCGGCTTCG ATCTAGAACT AGTGGATCCC CCGGGCTGCA GGAATTCGGC
   61 ACGAGCGGTT CCAAGTGGAC TTATTTTGGT CCTGATGGGG AGAATAGCTG GTCCAAGAAG
  121 TACCCGTCGT GTGGGGGCCT GCTGCAGTCC CCCATAGACC TGCACAGTGA CATCCTCCAG
  181 TATGACGCCA GCCTCACGCC CCTCGAGTTC CAAGGCTACA ATCTGTCTGC CAACAAGCAG
  241 TTTCTCCTGA CCAACAATGG CCATTCAGTG AAGCTGAACC TGCCCCTCGA CATGCACATC
  301 CAGGGCCTCC AGTCTCGCTA CAGTGCCACG CAGCTGCACC TGCACTGGGG GAACCCGAAT
  361 GACCCGCACG GCTCTGAGCA TACCGTCAGC GGACAGCACT TCTCCGCCGA GCTGCACATT
  421 GTCCATTATA ACTCAGACCT TTATCCTGAC GACAG?ACTG CCAGCAACAA GTCAGAAGAC
  481 CTCGCTGTCC TGGGTGCTCT CATTGAGATG GGCTCCTTCA ATCCGTCCTA TGACAAGATC
  541 TTCAGTCACC TTCAACATGT AAAGTACAAA GGCCAGGAAG CATTCGTCCC GGGATTCAAC
  601 ATTGAAGAGC TGCTTCCGGA GAGGACCGCT GAATATTACC GCTACCGGGG GTCCCTGATC
  661 ACACCCCCTT GCAACCCCAC TGTGCTCTGG GAAAACCCCGT GCAAATTTCC
  721 CAGGAGCAGC TGCTGGCTTT GGAGACAGCC CTGTACTGCA CACACATGGA CGACCCTTCC
  781 CCCAGAGAAA TGATCAACAA CT?CCCGGCAG GTCCAGAAGT TCG?TGAGAG GCTGGTATAC
  841 ACCTCCTTCT C?CAAGTGCA AGTCTGTACT GCGGCAGGAC TGAGTCTGGG CATCATCCTC
  901 TCACTGGCCC TGGCTGGCAT TCTTGGCATC TGTAATGTGG TGGTGGTGTC CATTTGGCTT
  961 TTCAGAAGGA AGAGTA?CCC C?AAAGGTGA TAACAAGGGA GTCATTTACA AGCCA?CCAC
 1021 CAAGATGGAG ACTGAGGCCC ACGCTTGAGG TCCCCGGAGC TCCCGGGCAC ATCCAGGAAG
 1081 GACCTTGCTT TTGGACCCTA CACACTTCGG CTCTCTGGAC ACTTGCGACA CCTCAAGGTG
 1141 TTCTCTGTAG CTCAATCTGC AAACATGCCA GGCCTCAGGG ATCCCTGCT
//
```

HODGKIN'S DISEASE ASSOCIATED MOLECULES AND USES THEREOF

RELATED APPLICATIONS

This application is a continuation-in-part of Ser. No. 08/644,116 filed May 10, 1996, which is a continuation-in-part of Ser. No. 08/580,980, filed on Jan. 3, 1996, which is a continuation-in-part of application Ser. No. 08/479,328, filed on Jun. 7, 1995, both of which are pending, and are incorporated by reference.

FIELD OF THE INVENTION

This invention relates to methodologies for identifying molecules of interest. In particularly preferred embodiments, the invention relates to the identification of molecules associated with pathological conditions such as cancer, (melanoma or renal cancer, e.g.), Hodgkin's Disease, autoimmune diseases and so forth. Also a part of the invention are the isolated molecules found as a result of the inventive method, such as presented peptides. These molecules include, inter alia, protein-containing molecules, isolated nucleic acid molecules encoding these, and antibodies which specifically bind to the protein-containing molecules. For convenience, the method described herein will be referred to as "serological fishing".

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from certain method of doing so. Another preferred method is the isolation of nucleic acid molecules which encode a particular marker, followed by the use of the isolated encoding molecule to express the desired molecule.

To date, two strategies have been employed for the detection of such antigens in, e.g., human tumors. These will be referred to as the genetic approach and the biochemical approach. The genetic approach is exemplified by, e.g., DePlaen et al., Proc. Natl. Acad. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines which are tested for the expression of the specific antigen. The biochemical approach, exemplified by, e.g., Falk et al., Nature 351: 290 (1991), and Kawakami et al., Nature 369: 69 (1994) both of which are incorporated by reference, is based on acidic elution of peptides which are bound to MHC-I molecules of tumor cells, followed by reversed-phase high performance liquid chromotography (R-HPLC). Antigenic peptides are identified after they bind to empty MHC-I molecules of mutant cell lines which are defective in antigen processing, and induction of specific reactions in cytolytic T-lymphocytes. These reactions include CTL proliferation, TNF release, and lysis of target cells, measurable in an MTT assay, or a $^{51}Cr$ release assay.

These two approaches to the molecular definition of antigens have the following disadvantages: first, they are enormously cumbersome, time-consuming and expensive; second, they depend on the establishment of cytolytic T cell lines (CTLs) with predefined specificity; third, their relevance in vivo for the course of the pathology or disease in question has not been proven, as the respective CTLs can be obtained not only from patients with the respective disease, but also from healthy individuals, depending on their T cell repertoire.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Brichard et al., J. Exp. Med. 178: 489–495 (1993); Coulie, et al., J. Exp. Med. 180: 35–42 (1994), Kawakami et al., Proc. Natl. Acad. Sci. USA 91: 3515–3519 (1994).

It would be desirable to have available a method which can be used not only for detection of tumor-associated antigens, but to determine molecules associated with any abnormal or pathological condition. Such a method would also facilitate the identification of such molecules, thereby enabling their use on the generation of, e.g., antibodies, cytolytic T cells, and so forth.

It is therefore the purpose of the present invention to develop methods and reagents for the simple detection and molecular characterization of antigens in human tissues, especially in tumor cells, which are useful in the molecular diagnosis of diseases and/or for immunotherapy and gene therapy of infectious, autoimmune and malignant diseases. The invention is delineated in the disclosure which follows.

BRIEF DESCRIPTION OF THE FIGURES

FIG. 3 shows, in bar graph form, the Northern Blot analysis of clone HOM-RCC-313 in renal cell carcinoma, normal kidney and other human tissues.

FIG. 4 shows the translated region of the gene coding for HOM-RCC-313. It is also SEQ ID NO: 4.

DETAILED DESCRIPTION OF PREFERRED EMBODIMENTS

Figure 1:
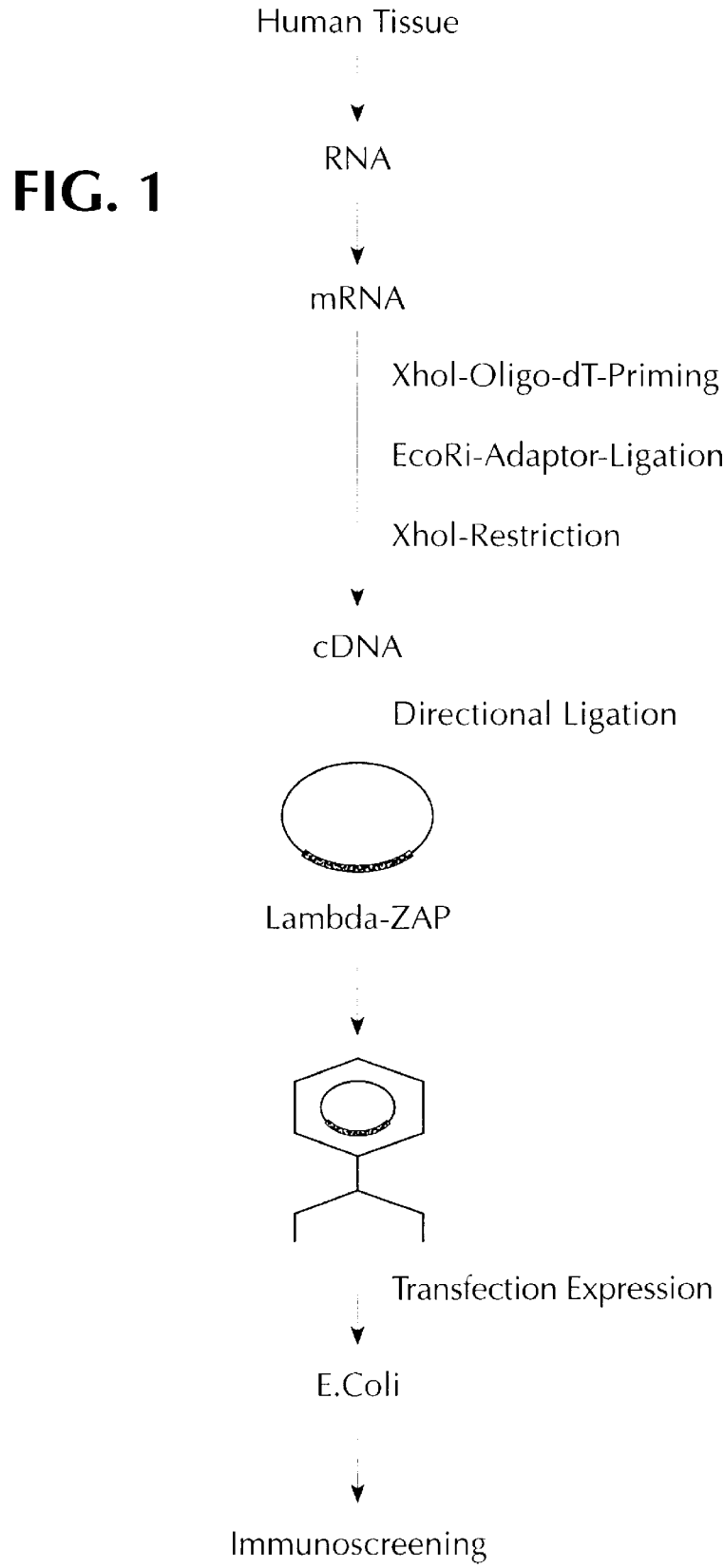
FIG. 1 shows the principles of the approach of the invention.

The following disclosure describes a methodology referred to as serological fishing. In it, a cell sample is taken from a subject afflicted with a pathological condition. The cells preferably are exemplary of the pathology. For example, if the subject has melanoma, the cells are melanoma cells. If the subject is suffering from a neural disorder, e.g., then the cells are preferably a sample of the afflicted cells. This approach is warranted because the afflicted cells are most probably the best source of protein-containing molecules of interest, i.e., such molecules which are specifically associated with the pathological condition of interest.

Note that cells representative of pathological conditions are not the only cells which may be used in the inventive method. It is very important, e.g., to ascertain those cellular "markers" associated with differentiation and maturation of cells, for example. The example of hematopoietic stem cells comes to mind. Similarly, the invention contemplates the isolation of, e.g., receptor molecules for specific ligands. In effect, one can assay for the presence of any molecule of interest using this methodology.

The cells chosen are then used to prepare a library of complementary DNA (i.e., "cDNA") . This methodology is well known to the skilled artisan, and need not be reiterated here. It is, of course, based upon the established fact that if proteins are expressed by the cells, then messenger RNA (mRNA) must be present at some point in time. These mRNA molecules are not long lived, and are unstable, so they are not practical to work with. The stability brought to the molecules when cDNA is used is very helpful to the method.

Once the CDNA is made, it is used to construct a vector library. In short, carrier vectors are treated, such as by cutting and splicing, to receive molecules of CDNA. The choice of vector may vary, as the skilled artisan is well familiar with many such examples.

Especially preferred are virus based vectors. In the case of eukaryotic cells, retrovirus or adenovirus based vectors are preferred. Such vectors contain all or a part of a viral genome, such as long term repeats ("LTRs") , promoters (e.g., CMV promoter, SV40 promoter, RSV promoter), enhancers, and so forth. When the host cell is a prokaryote, then bacterial viruses, e.g., phages, are preferred. Exemplary of such vectors are vectors based upon, e.g., lambda phage. In any case, the vector may comprise elements of more than one virus.

The resulting vectors are transfected or transformed into a host cell, which may be eukaryotic or prokaryotic.

Any cell normally used for transfection or transformation may be used in the protocol. Preferred materials include strains of *E. coli*, CHO cells such as CHO-1, COS cells such as COS-7, and so forth. Similarly, yeast cells, e.g., strains of Saccharomyces, strains of Pseudomonas, such as *Pseudomonas aeruginosa*, Bacillus bacteria, well known insect host cell *Spodoptera frugiperda*, and so forth, may all be used.

Once the recipient cells receive the vectors, they are cultivated so as to express foreign, protein containing molecules. "Protein-containing" is used herein because, while prokaryotes express only proteins, eukaryotic cells are well known for their ability to post-translationally modify proteins, so as to produce glycoproteins, lipoproteins, etc. It must also be borne in mind that "protein containing" as used herein, also encompasses peptides, such as the peptides presented by MHC molecules.

The processes now described below take place independently of the process described above, and no chronological relationship between the two facets of the invention is intended.

In pathological conditions such as cancer and, e.g., autoimmune diseases, there is some immune reaction to molecules associated with the pathology. This reaction can include an antibody response, B cell proliferation, proliferation of specific T cell subpopulations, increases in cytokine production, and so forth. The molecules and cells associated with the response may be found in body fluids of a subject, such as his or her serum. The immune responders will react with the molecule of interest whether it is produced recombinantly or autologously. The problem is to find them. As the examples show, this is done in a unique way. First, the body fluid, or other sample of interest, is reacted with a sample of the same host cells used for transfection or transformation. In this first step, the host cells are not transfected or transformed. The effect of this is to strip any immunogenic binding partners specific for the host cell rather than the targeted molecule. This step is necessary because, as was pointed out, supra, the host cell may be one against which the subject has developed an immune response at some point. This first stripping removes these immune components.

A second stripping step is then carried out. In this step, the previously stripped sample is now reacted with a sample of the same host cell as was described supra, this time having been transfected or transformed with the carrier vector lacking cDNA from the subject. The reason for this second stripping step is an observation made by the present inventor and not reported in the literature previously. The materials used as vectors, such as phages, viruses, etc., are useful because they naturally infect cells. Thus, *E. coli*, which inhabit the lower intestine of humans, are infected with lambda phage. It had not been considered, previously, that the immune response to *E. coli* includes a response to these infectious agents. Thus, applicants has surprisingly, achieved an ability to remove interfering immune components to an unprecedented degree by carrying out the two stripping steps. As noted, the first is against untransfected or untransformed host cells. The second is against host cells transfected or transformed with a vector which does not carry cDNA, wherein the vector is immunologically equivalent to the vector used to carry cDNA, as described supra.

It is especially preferred to carry out each of these stripping steps using a plurality of similar, but different procedures. The experiments which follow, for example, show absorption on a solid phase column, and then absorption on nitrocellulose paper. Applicant does not wish to be bound by any theory as to why the use of two similar but different protocols produce the results described herein. It is to be borne in mind, hereafter, that whenever "contacting a sample" is used herein, It is not to be limited to one contact step only, but may refer to more than one, preferably different, contact protocols designed to remove interfering binding partners from a sample under scrutiny.

It should be understood that these stripping steps may be done completely independently of the steps used to prepare the cDNA library. For example, if the test for an antigen is to be done at day "O", the stripping of sample may be done the day before, a week before, and so forth. One can also "bank" stripped sample from a donor or subject for future use.

The sample used is preferably serum, but need not be. Any sample which contains immunogenic binding partners may be so used.

In the next step of the method, lysed, transfected cells carrying the cDNA and expressing heterologous protein are contacted with the twice stripped sample. This sample should only contain immune components specific for the heterologous protein, and should bind thereto. This binding is facilitated if the cell lysates have been immobilized via contact to, e.g., activated filter paper, a solid phase column, etc., but this solid phase binding is not necessary, as the art will surely recognize that many, varied forms of assays are available for identifying a molecule of interest.

Once the immune component binds to the target molecule, a further step is desirably, but not necessarily, carried out.

This additional step involves the use of some binding partner for the first immune component, such as anti-IgG, carrying an identifiable label. The label may be a dye, an enzyme, a gold particle, a radiolabel, or any of the standard labels used in immunoassays.

Once identification is carried out, the immune components are removed, leaving the target molecule. The target molecule is then studied, using any of the standard methodologies in the art.

The artisan will note that the methodology also results in isolation of immune components which bind to the molecule of interest. Thus, in another aspect of the invention one can isolate antibodies, e.g., which are specific binding partners for the molecule of interest.

Yet another immune component which may be identified and isolated following the invention is a cytolytic T cell ("CTL" hereafter), specific for complexes of peptides derived from the identified molecule and MHC molecules to which these peptides bind, forming a complex. It is fairly well accepted that a CTL response involves the identification of complexes of MHC molecules and peptides, generally about 8-12 amino acids in length, but most preferably 9 or 10 amino acids in length, by T cell receptors ("TCRs") on the surface of circulating T cells. The TCRs react by binding to these complexes, "setting in motion," as it were, a series of reactions including the proliferation of CTLs specific for these complexes. One can produce and/or isolate such CTLs using the method of the invention, plus further steps.

As is pointed out in the examples which follow as well as the disclosure in general, one can easily identify cDNA encoding an antigen of interest. Once the cDNA is identified, one uses it to transfect host cells which either already present desired MHC molecules on their surface, or which have been transfected with DNA encoding these MHC molecules. The cDNA for the molecule of interest is expressed, and the molecule is processed to antigenic peptides which are presented by MHC molecules, such as HLA molecules. CTLs directed against the complexes are obtained from lymphocytes, such as autologous lymphocytes. From responder cell populations, long-term CTL clones are then obtained by the well known technique of limiting dilution. Once a positive CTL response is observed, the specific peptides presented to the CTLs are identified using established methods for example, screening the specific of previously identified CTL clones. Alternatively, the more recently described method of studying the sequence of the molecule of interest to identify potential MHC-binding motifs then analyzing these peptides, first for binding to the relevant MHC molecule and then, if positive for MHC-binding, for their ability to generate CTLs recognizing the peptide MHC complex may be used. Of course the peptides can also be eluted from the cells and sequenced, using well known techniques.

It will also be noted by the skilled artisan that one can correlate the expression of the molecule of interest back to a particular host cell or cells which expressed it. In so doing, one can remove the cDNA which expressed the molecule of interest, sequence it, and so forth. This aspect of the method is another feature of the invention.

Specific embodiments of the invention will be seen in the examples which follow. FIG. 1 depicts the method generally.

EXAMPLE 1

For the establishment of a cDNA library from human tissue total RNA was obtained from 0.5 ug of a renal clear cell carcinoma and established according to the method of Chomzynski, J. Analyt. Biochem. 162: 156–159 (1987), incorporated by reference. The mRNA was extracted from total RNA with oligo-dT-cellulose. The synthesis of the first strand cDNA was accomplished by the method described by Gubler and Hoffmann, Gene 25: 263 (1983) using RNase H and DNA polymerase I. For adaptation of the cDNA Klenow enzyme, adaptors with EcoRI restriction enzyme sites were ligated to the cDNA ends using T4 DNA ligase (Ferretti L and Sgamerella V, Nucl. Acids Res. 9: 3695 (1981)). Following restriction enzymatic digestion with the enzyme XhoI, cDNA molecules of different length were separated using Sephacryl 400 and transfected into λZAPII phage vectors (Short et al., Nucleic Acids Res. 16: 7583 (1988)). The recombinant phage DNA was packed into phages after ligation with packing extracts and used for the transfection of $E.\ coli$ bacteria. The titration of the library resulted in $1.8\times10^6$ recombinant primary clones. The total cDNA library was transfected in $E.\ coli$ and amplified. The titer of the CDNA library after amplification was $10^{11}$ plaque forming units per ml (pfu/ml). These transfected cells were used in experiments which follow.

EXAMPLE 2

In accordance with the invention as described, supra, identification of immunogenic material was achieved by using human sera which have been completely depleted of antibodies directed against antigens derived from native and lytic λ phage-transfected $E.\ coli$ bacteria. To this end, the serum was "stripped" via absorption, as now described.

$E.\ coli$ bacteria of the strain XL1-Blue were cultured in 50 ml LB medium overnight. After achieving an optical density of $OD_{600=1.0}$, the bacteria were pelleted by centrifugation, resuspended in 5 ml phosphate buffered saline (PBS), and sonicated by ultrasound to form a lysate. The bacterial lysate was bound onto a matrix of activated Sepharose, which was then put into a column and used for the absorption of the human serum. The serum was run over this column 10 times.

A culture of $E.\ coli$ XL1-Blue bacteria in the exponential growth phase was pelleted by centrifugation, transfected in 0.01 M magnesium sulfate with 106 XZAPII phages without a recombinant insert and incubated in 5 ml LB medium for four hours. The lysate of the transfected bacteria was used in the same manner as the untransfected bacteria, with the human serum described supra being passed through the column an additional ten times.

To complete the depletion of the serum, interfering antibodies from lytically transfected $E.\ coli$ bacteria were cultured on agar plates (10 hours, 37° C.) and their proteins were blotted onto nitrocellulose membranes after this culturing step. Following this, the serum which had been preabsorbed according to the above steps was transferred to the blotted nitrocellulose membrane, and the absorption procedure was repeated five times. The serum, which was processed in accordance with the invention, was totally depleted of antibodies directed against antigens derived from $E.\ coli$ and phages.

EXAMPLE 3

In these experiments, a renal cancer-specific antigen was identified via the following steps. Bacteria of the strain $E.\ coli$ XL1-Blue were transfected with recombinant phages derived from the described cDNA library and plated at a density of $4–5\times10^3$ plaque forming units (PFUs) per plate in LB-medium with isopropylthiogalactopyranoside ("IPTG"). After 12 hours of incubation at 37° C, nitrocellulose membranes were put on top of the cultures, and the culture plates were incubated for another four hours. This was followed by incubation of the nitrocellulose membrane for one hour in Tris-buffered saline (TBS) with 5% milk powder. After washing the nitrocellulose membranes three times in TBS, the stripped human serum secured following Example 2 was diluted 1:1000 in TBS/0.5% milk powder (w/v) and incubated overnight with gentle shaking. After the incubation with the nitrocellulose membrane the serum was removed and kept for additional testing. Following incubation with serum, the nitrocellulose membranes were washed three times in TBS, and incubated with polyclonal alkaline phosphatase-conjugated goat anti-human IgG for one hour. Following this, the nitrocellulose membranes were washed repeatedly with TBS/0.01% Tween 20 (v/v)). The reaction was developed using nitroblue tetrazolium chloride and bromochloro-indoyl-phosphate in TBS. The binding of human antibodies to the expressed protein became visible by a blue, ring-formed color deposit on the nitrocellulose membrane. The efficient preabsorption of the serum made it possible to develop the membrane at 37° C. over several hours without compromising the quality of the test because of background reactivity caused by antibodies against $E.\ coli$ and phage antigens.

Positive clones were localized on the agar plates, transferred into transfection buffer, and used for a second round of transfection and subcloning. A total of $1.8 \times 10^6$ recombinant clones were subjected to screening and five different positive-reacting clones were identified.

EXAMPLE 4

Figure 2:
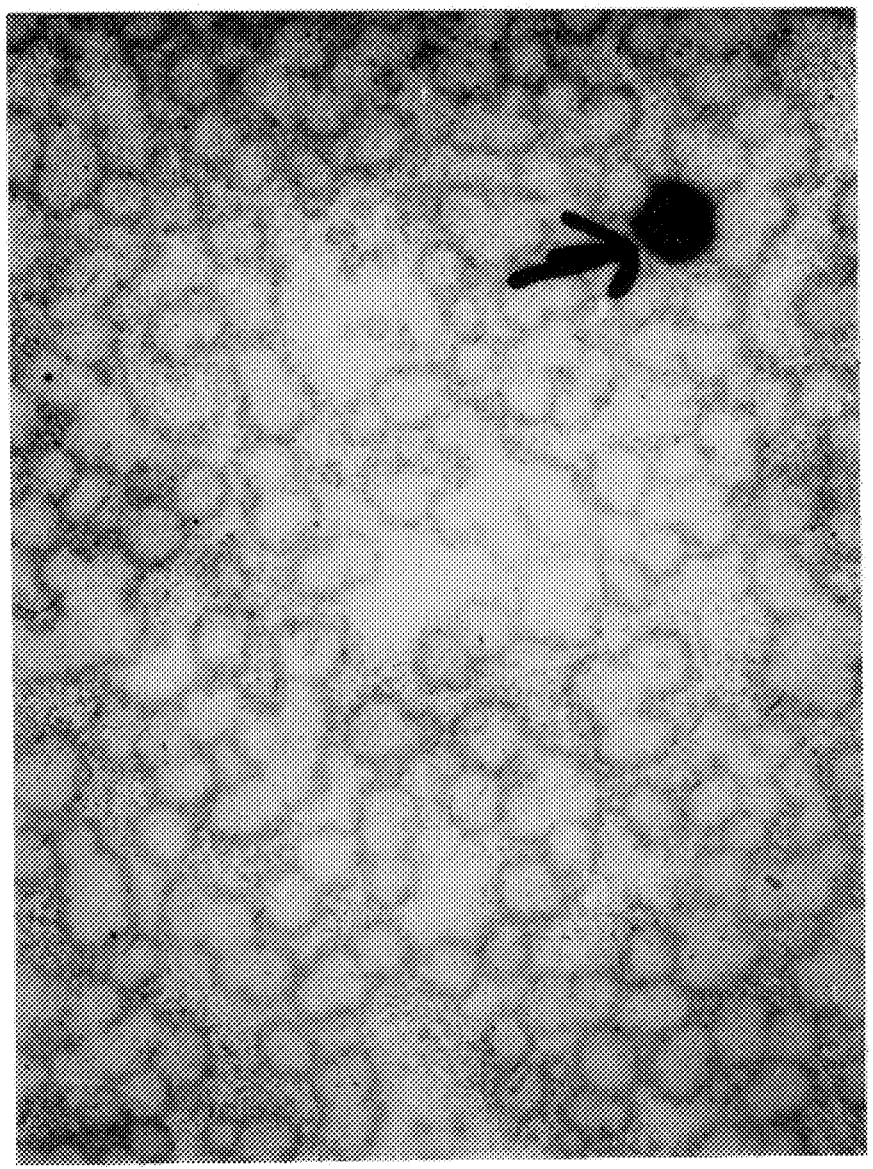
FIG. 2 shows a nitrocellulose membrane with a positive clone derived from the cDNA of a renal cell clear carcinoma that reacts with a 1:100 dilution of the patient's serum.

Positive clones secured following Example 3, i.e., those which had bound antibodies derived from the processed human serum, were subcloned to monoclonality by repeated rounds of transfection and testing of reactivity with the processed human serum. P-bluescript phagemids with the respective cDNA inserts were cloned by in vivo excision (Hay and Short, Strategies 5: 16–19, 1992) from the λZAPII phage vectors and used for transfection of $E.\ coli$ SOLR bacteria. Plasmids were isolated from the bacteria after alkaline lysis with NaOH in a modification of the method of Birnboim and Doly, J. Nucl. Acids Res. 7: 1513 (1979). The recombinant plasmid DNA was sequenced according to the classic method of Sanger (Proc. Natl. Acad. Sci. USA 74: 5463 (1977)) using M13-forward and M13-reverse oligonucleotides. The DNA sequence obtained and the resulting amino acid sequence were checked for in nucleic acid and protein data banks (Gene Bank, EMBL, Swiss Prot). The sequencing of the cDNA inserts was continued using internal oligonucleotides. Analysis showed no homology with any sequences deposited in the data banks. The full length cDNA clone referred to as SK313, which had been cloned with the RACE method (Frohman MA, Dush MK, Martin GR, Proc. Natl. Acad Sci. USA 85: 8998 (1988)), had a carbonic anhydrase domain at the 5' end. The nucleic acid sequence of this molecule is presented in SEQ ID NO: 1. FIG. 2 shows a nitrocellulose membrane with a positive clone from these experiments.

EXAMPLE 5

As a follow up to these experiments, RNA was isolated from a spectrum of malignant and normal human tissues according to the method of Chomzynski and Sacchi, Analyt Biochem. 162: 156 (1987).

After denaturation, the total isolated RNA was separated on an agarose gel containing 1% formaldehyde by electrophoresis (Goldberg, Proc. Natl. Acad. Sci. USA 77: 5794 (1980)) and then blotted onto a nylon membrane according to a known method (Seed, Nucl. Acids Res. 10: 1799 (1982)) Radiolabeled cDNA inserts of the identified clones were used for hybridization. The hybridization was carried out according to a known method (Geoffrey and Berger, Enzymol. 152: 419 (1987)) . The presence of the respective RNA was demonstrated using autoradiography and X-ray films. The analysis demonstrated that the mRNA of clone HOM-RCC-313 was overexpressed in 4 out of 19 renal cell carcinomas compared to normal kidneys. Very weak expression was found only in colonic mucosal tissue and in normal kidney. Expression in other tissues could not be demonstrated.

EXAMPLE 6

To determine the incidence of antibodies against antigens which are identified in accordance with the invention, sera from healthy individuals and tumor patients were analyzed. To this end, the sera were processed as described, supra, and depleted of antibodies against antigens derived from $E.\ coli$ and phages. For the detection of antigen-specific antibodies, phages derived from reactive clones were mixed with non-reactive phages derived from the same cDNA library at a ratio of 1:10 and tested as described supra, for reactivity with antibodies in the human test serum. The serum which had been used for the identification of the antigen was used as a positive clone. The non-reactive phages served as a negative control. A serum sample was positive for antigen reactive antibodies, if the expected percentage of the phage plaques showed a positive reaction. In the case of the renal cell carcinoma antigen represented by clone HOM-RCC-313, the analysis of a spectrum of human sera showed that only sera from renal cell carcinoma patients contained reactive antibodies. Sera from healthy controls and patients with other tumors did not contain such antibodies.

The cDNA for clone HOM-RCC-313 was excised from the plasmid DNA by digestion with the restriction enzyme EcoRI, and separated by agarose gel electrophoresis, followed by extraction from the gel. This was then used to create a vector which expresses a fusion protein with the bacterial protein anthranilate synthetase. A relevant fragment in the exact open reading frame was cloned into pATH plasmid vectors (Koerner, et al, Meth. Enzymol. 194: 477 (1991). Induction of protein expression was obtained after transformation of the plasmids into $E.\ coli$ of strain BL21 as described (Spindler, et al, J. Virol. 49: 132 (1984)). Expressed, fusion proteins were separated by SDS gel electrophoresis, excised from the gel, eluted and freeze dried. Rabbits were immunized by subcutaneous injection with 100 μg of the lyophilisate dissolved in Freund's adjuvant. Immunization was repeated three times at two-week intervals using incomplete Freund's adjuvant. The rabbit was bled and antiserum was obtained. The obtained antiserum was depleted from antibodies reactive with $E.\ coli$ and phages in the manner described supra and tested for reactivity against the renal carcinoma antigen as described for the human serum. Reactivity was detected at dilutions of 1:>100,000.

EXAMPLE 7

The protocols set forth in the preceding examples were followed, using biopsied tissue taken from different subjects suffering from (i) malignant melanoma, (ii) astrocytoma, and (iii) Hodgkin's Disease. Table 1, which follows, summarizes the results, including those obtained with the renal cancer study, set out in detail in Examples 1–6, supra.

TABLE 1

Antibody reactivity of autologous sera with recombinant clones derived from human tumor cDNA. cDNA libraries were screened with autologous patient serum. Positive clones were subcloned to monoclonality. Inserts from each clone were amplified with plasmid primers and separated by agarose gel electrophoresis. Southern blots were performed by cross hybridization with the respective inserts.

| tumor | clones tested | positive clones | different inserts |
|---|---|---|---|
| malignant melanoma | $1.0 \times 10^6$ | 40 | 10 |
| renal cell carcinoma | $1.8 \times 10^6$ | 7 | 5 |
| astrocytoma | $1.2 \times 10^6$ | 49 | 5 |
| Hodgkin's disease | $1.0 \times 10^6$ | 14 | 4 |

2 summarizes these assays. In these studies, phages from positive clones were mixed with non-reactive phage (ratio:1:10), and then used to transfect bacteria (*e. coli*). Dilutions of patient sera (1:200), were used, in an enzyme linked immunosorbent assay (ELISA), as described supra. "HOM-MEL-40" refers to the new melanoma antigen (SEQ ID NO: 2), while "HOM-MEL-55" refers to MAGE-1 (van der Bruggen et al., supra). "HOM-RCC 3.1.3" is the renal cancer antigen of SEQ ID NO: 1. "HOM-GLO-30.2.1" refers to the previously identified astrocytoma associated antigen, "HOM-HD-21" refers to the new, lectin-like antigen of SEQ ID NO: 3, and "HOM-HD-397" is the previously identified restin antigen.

TABLE 2

Humeral immune responses against human tumor antigens. Phages from positive clones were mixed with nonreactive phages of the cDNA-library at a ratio of 1:10 and used to transfect bacteria. IgG antibodies to the clones were detected with an enzyme-linked assay using 1:200 diluted patient sera. n.t. = not tested

| antigen identity/homology | HOM-MEL-40* | HOM-MEL-55 NAGE-1 | HOM-ROC-3.1.3* CAH-like | HOM-GLIG-30.2.1 tegt | HOM-HD-21* lectin-like | HOM-HD-397 restin |
|---|---|---|---|---|---|---|
| melanoma patients | 2/11 | 4/11 | n.t. | n.t. | n.t. | n.t. |
| recal cancer patients | 0/8 | 0/8 | 2/14 | 0/7 | 0/7 | 5/7 |
| astrocytoma patients | 0/10 | 0/10 | 0/11 | 2/13 | 0/11 | 7/11 |
| Hodgkin's patients | 0/10 | 0/10 | 0/17 | 0/17 | 10/18 | 14/17 |
| healthy controls | 0/12 | 0/12 | 0/15 | 0/20 | 0/17 | 12/17 |

Analysis of the different inserts showed that the melanoma cells expressed the known tumor rejection antigen precursor MAGE-1 (see van der Bruggen et al., Science 254: 1643-7 (1991), incorporated by reference), as well as a new antigen. A portion of the cDNA sequence of this antigen is set forth in SEQ ID NO: 2.

When the astrocytoma study was completed, the observed insert appeared to correspond to the previously described Tegt gene (Old, Canc. Res. 41: 361–375 (1981), incorporated by reference).

When the Hodgkin's Disease study was completed, a previously unknown antigen was isolated, and cDNA encoding it was identified in the library, using standard methods. The antigen is a newly observed, lectin-like structure, a portion of the cDNA for which is set forth in SEQ ID NO: 3. Also observed were antibodies against restin, described by Bilbe, et al, EMBO J 11: 2103-13 (1992). This is an intermediate filament associated protein, expression of which has been shown to be restricted to Hodgkin and Reed-Sternberg cells, as well as cultured monocytes.

EXAMPLE 8

A further study of occurrence of antibodies against the antigens described in Examples 1–7 was carried out. Table The fact that antibodies against the tumor antigens, excepting only restin, were detected, albeit at varying rates, only in the sera of patients diseased with the same type of tumor suggests that tumor growth is essential for the development of a humoral response against tumor antigens.

The reason for the presence of restin in healthy controls is not clear. One may speculate that tolerance against respective antigens might be circumvented, because the antigen may have similar sequences to another antigen, the donor may have premalignant cells, or the antigen may be activated in normal cells under non-malignant conditions, such as viral infections, or other inflammatory processes.

EXAMPLE 9

In order to determine the expression pattern of the newly identified antigens described herein, Northern blot analysis was carried out, using a variety of human tissues.

RNA was extracted from tissue samples (tumor and normal) using the well known guanidium isothiocyanate/phenol/chloroform method of Chomzynski, et al., supra. The RNA integrity was checked via electrophoresis in formalin/MOPS gels. Then, gels containing 40 ug of RNA per lane were blotted onto nylon membranes. These Northern blots were then probed with the cDNA of SEQ ID NO: 1, 2 or 3. Hybridization was with $^{32}P$ labelled probes at 42° C., with formamide. The filters were washed at 65° C., at 1×SSC, 0.2% SDS, and exposed for 16 hours. These are "stringent conditions" as defined hereafter. After exposure, filters were stripped and rehybridized with GAPDH.

Table 3 summarizes these results.

TABLE 3

Expression pattern of tumor antigens in various tissues (selection). Northern-slot analysis was performed with RNA samples from tumor and normal human tissues matched by hybridization with GAPDH. Expression ratios were calculated after densitometric analysis of eutoradiographs. The signal obtained with the normal counterpart of the diseased tissue was set to 1. n.t. = not tested;

| antigen identity/homology | HOM-MEL-40* | HOM-RCC-3.1.3* CAH-like | HOM-GLIO-30.2.1 Tegt | HOM-HD-21* Lectin-like |
|---|---|---|---|---|
| kidney | – | 1 | 1.5 | — |
| brain | – | n.t. | 1 | n.t. |
| tonsil | – | — | 1 | 1 |
| stomach | – | — | 1.5 | — |
| colon mucosa | – | 0.2 | 1.5 | — |
| breast | – | — | 1.0 | — |
| recal cancer | – | >5 in 4/19 cases ≦1 in 15/19 cases | n.t. | — |
| Hodgkin's tissue | n.t. | — | n.t. | >10 |
| asatrocytoma | n.t. | n.t. | >5 in 8/12 1 in 4/12 | — |
| melanoma | ++ | — | n.t | — |

As will be seen, the new melanoma associated antigen is strongly expressed in melanoma, but not other tissues. Carbonic-anhydrase-like antigen was strongly expressed in about 20% of renal cell carcinomas, and only weakly in normal renal tissue. Tegt was overexpressed on 8/12 astrocytoma tissues compared to normal brain tissue. The mRNA for the lectin like molecule associated with Hodgkin's disease was increased about ten fold in diseased tonsils as compared to normal tonsils, suggesting that overexpression may be a frequent characteristic of proteins which elicit autologous B cell responses.

EXAMPLE 10

Further studies were carried out on the HOM-MEL-40 sequence. Using standard genetic analysis techniques, the 5' region of the mRNA for HOM-MEL 40 was shown to have a tyrosine kinase binding domain. This suggests that HOM-MEL-40 may function as a receptor. The 3' portion of the RNA is identical with an RNA molecule for "SSX," a molecule known to be involved in the SYT-SSX translocation in synovial tumors.

EXAMPLE 11

Additional experiments were also carried out to study HOM-MEL 40. Standard Northern blotting showed that, with the exception of testis, HOM-MEL 40 was not expressed in normal tissues. In contrast, it was expressed in 50% of melanomas, 20% of prostate cancers, 20% of gastric cancers, 26% of colorectal cancers, 12% of the lung cancers and 20% of breast and hepatacellular cancer. It was also found in 1/10 gastric, and 1/5 thyroid carcinomas.

Additional Western blotting work was carried out, showing that antibodies against HOM-MEL 40 were present in 10 of 89 melanoma patients tested, but only 3 out of 49 healthy male subjects.

In yet further studies, it was observed that HLA-A2 positive tumor cells presented a nonamer derived from HOM-MEL. This suggests that HOM-MEL 40 specific vaccines, useful in inducing CTLs, are possible.

EXAMPLE 12

The phage assay described in the prior examples is not appropriate for screening large numbers of serum samples. In order to do so, a modification of the standard Western Blot was developed. This variation is based upon His-tagged, recombinant HOM-MEL 40, as is herein described.

HOM-MEL-40 was amplified, over 20 cycles, using pfu polymerase, on plasmid cDNA prepared from melanoma tissue. The oligonucleotide primers used were:

5'-GCCAAATACTTCTCTAAGGAAGAGTGG-3' (SEQ ID NO: 5); (sense)

5'-TTCACTGTTGTGAACACTTGCTTTCAC-3' (SEQ ID NO: 6); (antisense) Polymerase chain reaction (PCR) was carried out at 95° C./1 minute; 60° C./1 minute; and 72° C./1 minute, followed by a final extension at 72° C for 10 minutes. The amplification product was gel purified, using art recognized techniques, and then ligated in frame to SmaI digested, dephosphorylated and gel purified pQE32 vector. This results in production of a fusion protein having a "tail" of 6 histidine molecules at the N-terminus.

The construct was then transformed into $E.$ $coli$ SG13009 (pREP4) strain, followed by selection on plates containing kanamycin and ampicillin. Individual colonies were picked, and expressed on a small scale by inducing these with 2 mM isopropyl thiogalactoside (IPTG). This permits checking for protein expression. Small scale purification over Ni-NTA columns was then performed, for each clone.

One clone was identified as expressing a protein of expected length. This clone was isolated and sequenced using well known techniques. It was verified as HOM-MEL 40. Following the identification, large scale induction of recombinant protein was carried out. Specifically, cells were induced with 2 mM IPTG, and harvested five hours later. Cells were lysed, by combining with a buffer of 8 M urea, 100 mM $Na_2PO_4$, 10 mM Tris ·HCl (pH8), 0.01% Triton X, overnight. Any cellular debris was spun down, and supernatant was loaded onto pre-equilibrated Ni-NTA resin. Washes were performed with two volumes of the aforementioned buffer, at pH8, and then at least 10 volumes of the buffer, at pH6.3. Protein was then eluted, using the buffer described herein, plus 250 mM imidazole. Yields ranged from 15 to 40 mg of His-tagged protein per liter of bacterial culture.

Western blotting was then carried out, using the His-labeled protein. In these assays, 5 ug of recombinant His-tagged proteins, which served as internal negative controls, were mixed with 2×SDS sample buffer (0.1 M Tris-HC1, pH 6.8, 0.2M dithiothreitol, 4% SDS, 0.2% bromophenol blue, 20% glycerol), and were then electrophoresed in 12% SDS- PAGE, followed by blotting to nylon membranes using semi-dry transfer.

After blocking of any unspecified binding with 5% low fat milk in PBS (1 hour), membranes were incubated with 1:100 diluted sera from tumor patients or healthy controls. Blots were then incubated for one hour with alkaline phosphatase conjugated mouse anti-human IgG. The membrane was then incubated, consecutively, with rabbit anti-mouse IgG (30 minutes), anti-alkaline phosphatase, and then 0.25 mg/ml of alkaline phosphatase. After each incubation step, the membranes were washed extensively with TBS and 0.1% Tween. Visualization was performed by staining with 5-bromo-4-chloro-3-indolyl-phosphate (BCIP), and nitroblue tetrazolium. The sera were analyzed in random order (healthy/melanoma positive), with the observer blind to the status of the sample. All analyses were carried out in duplicate.

The blotting showed a product with a molecular weight of about 24 kD by SDS-PAGE, which is consistent with a calculated molecular weight of 21.6 kD, based upon predicted amino acid sequence.

The immunoblotting described supra, was carried out on 89 melanoma samples, six ovarian cancer samples, and ten renal carcinoma samples. Of these, 11 melanoma samples, one ovarian cancer sample, and three renal cell carcinoma samples were positive. Sera from subjects with colorectal, lung, breast, gastric, or pancreatic cancer were negative. A total of 41 healthy controls were also analyzed, of which three were positive. Any sera which were reactive in the Western blot, as well as twenty negative serum samples were then reassessed, using the phage assay, described supra. The reactivity was confirmed for 10 of the 11 melanoma patients and the positive ovarian cancer patient. The renal cell cancer patient and the healthy controls were negative, and were all samples negative in the Western blot.

There were 16 melanoma patients who provided both serum and tumor specimens. It was found that HOM-MEL 40 expression by the tumor could be compared with antibody reactivity in the sample. As will be seen in the table which follows, eight of the sixteen patients had HOM-MEL-40 positive tumors, but only three had antibodies against the antigen in their serum. No antibodies were detected in the serum of patients with HOM-MEL-40 negative tumors.

EXAMPLE 13

The result observed in Example 7 were of interest, and additional experiments were then carried out.

The serological analysis described supra was carried out on various Hodgkin's Disease cell samples. One cDNA clone, identified using the methods described supra, was compared to the known cDNA sequence for restin, and was found to correspond to a truncated form of the known cDNA. Specifically, the truncated cDNA, presented herein as SEQ ID NO: 7, encodes for a protein truncated at the carboxy terminus, leading to disruption of the a-helical rod domain. This domain is known to be important for the formation of filaments.

Northern blot analysis was carried out, using protocols set forth supra, and this analysis showed that the transcript was specifically expressed in Hodgkin's Disease associated tissues, but not normal tissues.

These results were then confirmed, using single cell RT-PCR, using transcript specific oligonucleotides.

A final set of confirming experiments were carried out via Western blotting, using polyclonal antibody serum which was produced using recombinantly produced antigen.

EXAMPLE 14

Rammensee, et al., Immunogenetics 41: 178–228 (1995), incorporated by reference, disclose many peptides which bind to HLA-A2.1, and some which also provoke CTL proliferation. Some of these are of formula:

XaaLeu(Xaa)$_6$ (Ile, Leu,Val)   (SEQ ID NO: 8 ).

The deduced amino acid sequence for HOM-MEL 40 was screened for sequences which might act as HLA-A2.1 binders/CTL stimulators, and the following were found:
Arg Leu Gln Gly Ile Ser Pro Lys Ile (SEQ ID NO: 9);
Arg Leu Arg Glu Arg Lys Gln Leu Val (SEQ ID NO: 10);
Lys Ile Gln Lys Ala Phe Asp Asp Ile (SEQ ID NO: 11)
These peptides were synthesized, using well known techniques and Fmoc protected amino acids. The peptides were then purified, using Sephadex G25, followed by reverse phase HPLC on a C-18 column. T2 cells, which are deficient in transporters associated with antigen presentation (DeMars, et al., Proc. Natl. Acad. Sci. USA 82: 8183 –8187 (1985); Slater, et al., Immunogenetics 21: 235–241 (1990)), were used in peptide binding assays, as follows. A sample of 5×10$^5$ T2 cells were incubated for 4 hours at 37° C., in the presence or absence of 100 uM of the HOM-MEL-40 peptides. Positive controls were an EBV LMP2 derived peptide:
Cys Leu Gly Gly Leu Leu Thr Met Val (SEQ ID NO: 12) and
an HIV reverse transcriptase derived peptide:
Ile Leu Lys Glu Pro Val Gly Val (SEQ ID NO: 13)
Upregulation of HLA-A2.1 on T2 cells was measured by labelling with an anti-HLA-A2.1 specific monoclonal antibody (i.e., BB7.2), followed by incubation with an FITC conjugated goat anti-mouse antibody. The samples were analyzed by flow cytometry, with upregulation of HLA-A2.1 being given by the ratio:

$$\frac{\text{mean fluorescence intensity in sample with peptide}}{\text{mean fluorescence intensity in sample without peptide}}$$

Each of the three peptides were seen to bind to HLA-A2.1, with SEQ ID NO: 9 showing strongest HLA-A2.1 upregulation by far, as determined by FACS analysis.

As the foregoing shows, the invention relates to a method for determining or isolating an immunoreactive substance. "Immunoreactive substance" as used herein refers to any material which provokes some form of immune response in the subject which produces it. This response may be based upon either a B cell or a T cell response. Such immunoreactive substances include proteins, peptides, glycoproteins, lipoproteins, peptide containing complexes (e.g., MHC/peptide complexes), antibodies, and so forth. To determine such substances, a cDNA library is prepared from cells of a subject, using well known, standard methods. The cDNA is then inserted into an appropriate vector, such as a eukaryotic cell specific virus or a phage (i.e., a bacterial virus), to form a transfecting/transforming library, which is then incorporated into a host cell. The host cells are treated so that they express the library component (cloned cDNA) they receive. The host cells are then lysed, so that the expressed material is available for further treatment.

The lysed material is then contacted with a "stripped" sample believed to contain an immunogenic binding partner for the immunoreactive substance. "Immunogenic binding partner" as used herein refers to any immune system associated material which binds to the target, i.e., the immunoreactive substance. Such binding partners include, but are not limited to, antibodies, T cells, cytokines, ligands, receptors, and so forth, as well as truncated portions of these molecules, complementary nucleic acid molecules, and so forth. Note that for some of these components, such as T cells, further steps including those recited herein are required.

The stripped sample, as indicated supra, has been treated by contact with both (i) non-transfected or transformed host cells, and (ii) host cells transfected or transformed with vectors which do not contain the pertinent cDNA.

The stripped sample is useful for identifying binding partners for the expressed material because many of the immune components which would otherwise interfere with the specific immunological reaction desired have been removed via the absorption steps described herein.

The identification of the expressed material may be followed by isolation of the cDNA encoding it. One can punch holes through a membrane such as a nitrocellulose membrane, placed on top of Petri dishes containing colonies of host cells, then use the immune reaction to give position on the solid phase. Each colony is based upon limited cDNA transfection, thereby facilitating isolation and identification of relevant cDNA.

The invention also relates to the isolated nucleic acid molecules of SEQ ID NO: 1, 2, 3 or 7 which encode for molecules which are associated with particular conditions. In addition to their role as coding materials, these molecules can also be used as probes to identify cells expressing the relevant antigens, as it has been shown that these cDNA molecules (SEQ ID NO: 1, 2, 3, and 7) are based upon mRNA which translated to the antigen.

Also a part of the invention are isolated nucleic acid molecules, the complementary sequences of which hybridize to one of SEQ ID NO: 1, 2, 3 or 7, and which encode a protein equivalent to those encoded by SEQ ID NO: 1, 2, 3 or 7. "Stringent conditions" as used herein, refers to conditions at least as stringent as hybridization at 50 $\mu$l/cm$^2$ of 3.5×SSC, 1×Denhardt's solution, 25 mM sodium phosphate buffer (pH 7.0), using a $^{32}$P– labelled probe, for 18 hours at 65° C., followed by four washes (one hour, each wash, at 65° C., 2×SSC, 0.1% SDS), and a final wash for 30 minutes at 1.0×SSC 0.2% SDS. The final wash can be changed to 0.5×SSC to 0.2×SSC, or even 0.1×SSC, and SDS can be lowered to 0.1% to increase stringency, if desired.

The invention also includes those peptides associated with tumor antigens, such as those of SEQ ID NOS: 9, 10 and 11, which bind to HLA-A2.1 molecules, thereby provoking lysis by cytolytic T cells. Also a part of the invention are peptides of formula Xaa Leu Xaa$_7$ (SEQ ID NO: 14)

wherein the sixth amino acid residue is Ser, Lys or Phe, and the ninth amino acid residue is Val or Ile. These molecules can also serve, very simply, as markers for HLA-A2.1 cells, as it is well known that peptide/MCH complex formation is quite specific.

Other features of the invention will be clear to the skilled artisan and need not be reiterated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

I claim:

1. Isolated nucleic acid molecule consisting of the nucleotide sequence of SEQ ID NO: 7.

2. An isolated recombinant cell comprising the isolated nucleic acid molecule of claim 1.

3. Isolated nucleic acid molecule which encodes a protein consisting of an amino acid sequence identical to the amino acid sequence encoded by SEQ ID NO: 7.

4. An isolated recombinant cell comprising the isolated nucleic acid molecule of claim 3.

5. Expression vector comprising an isolated nucleic acid molecule which consists of SEQ ID NO: 7, operably linked to a promoter, wherein said isolated nucleic acid molecule encodes a protein identical to the protein encoded by SEQ ID NO: 7.

6. An isolated recombinant cell comprising the expression of claim 5.

7. Expression vector comprising an isolated nucleic acid molecule which encodes a protein which consists of the nucleotide sequence of the isolated nucleic acid molecule of claim 3, and encodes the protein encoded by SEQ ID NO: 7, operably linked to a promoter.

8. An isolated recombinant cell comprising the expression vector of claim 7.

9. A method for screening for possibility of Hodgkin's disease, comprising contacting a cell sample from a subject with an isolated nucleic acid molecule which hybridizes, under stringent conditions to the nucleic acid molecule having the nucleotide sequence of SEQ ID NO: 7, and determining hybridization of said isolated nucleic acid molecule to a target nucleic acid molecule as an indication of possible Hodgkin's Disease in said subject.

10. The method of claim 9, wherein said isolated nucleic acid molecule consists of SEQ ID NO: 7.

11. An isolated nucleic acid molecule which encodes a Hodgkin's Disease specific antigen, the complementary sequence of which hybridizes, under stringent conditions, to the nucleotide sequence of SEQ ID NO: 3.

12. The isolated nucleic acid molecule of claim 11, consisting of the nucleotide sequence of SEQ ID NO: 3.

13. An isolated recombinant cell comprising the isolated nucleic acid molecule of claim 12.

14. Expression vector comprising an isolated nucleic acid molecule which consists of the nucleotide sequence of the isolated nucleic acid molecule of claim 11 and encodes a protein consisting of an amino acid sequence identical to the amino acids encoded by said nucleic acid molecule, operably linked to a promoter.

15. An isolated recombinant cell comprising the expression vector of claim 14.

16. An isolated recombinant cell comprising the isolated nucleic acid molecule of claim 11.

17. Expression vector comprising an isolated nucleic acid molecule which encodes a protein which consists of an amino acid sequence identical to the amino acid sequence encoded by SEQ ID NO: 3, operably linked to a promoter.

18. An isolated recombinant cell comprising the expression vector of claim 17.

19. A method for screening for possibility of Hodgkin's disease, comprising contacting a cell sample from a subject with an isolated nucleic acid molecule which hybridizes, under stringent conditions to the nucleic acid molecule having the nucleotide sequence of SEQ ID NO: 3, and determining hybridization of said isolated nucleic acid molecule to a target nucleic acid molecule as an indication of possible Hodgkin's Disease in said subject.

* * * * *

UNITED STATES PATENT AND TRADEMARK OFFICE
CERTIFICATE OF CORRECTION

PATENT NO. : 5,840,568          Page 1 of 2

DATED : November 24, 1998

INVENTOR(S) : Michael Preundschuh

It is certified that error appears in the above-identified patent and that said Letters Patent is hereby corrected as shown below:

In the cover page, under the section entitled Appln No.:, change "668,128" to read as - - 08/668,128 - -.
In column 1, line 4, change "both" to read as - - all - -.
In column 4, line 41, change "It" to read as - - it - -.
In column 6, line 19, change "CDNA" to read as - - cDNA - -.
In column 6, line 41, change "106 XZAPII Phages" to read as - - $10^6$ λZAPII phages- -.

In column 11, Table 2, 3rd column, 2nd row change "recal" to read as - - renal - -.
In column 11, Table 3, 1st column, 11th row change "≤" to - - $\leq$ - -.
In column 11, Table 3, 1st column 11th row, change "asatrocytoma" to read as - - astrocytoma - -.

UNITED STATES PATENT AND TRADEMARK OFFICE
CERTIFICATE OF CORRECTION

PATENT NO. : 5,840,568

DATED : November 24, 1998

INVENTOR(S) : Michael Pfreundschuh

It is certified that error appears in the above-identified patent and that said Letters Patent is hereby corrected as shown below:

In column 12, line 25, change "HOM-MEL-40" to read as - - HOM-MEL 40 - -.
In column 13, line 40, change "HOM-MEL-40" to read as - - HOM-MEL 40 - -.
In column 13, line 52, change "a-helical" to read as - - $\propto$-helical - -.
In column 31, line 34, insert "vector" after the word expression
to read as - - expression vector - -.

Signed and Sealed this

Ninth Day of January, 2001

Attest:

Attesting Officer

Q. TODD DICKINSON

Commissioner of Patents and Trademarks

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
        ( A ) LENGTH: 2679 base pairs
        ( B ) TYPE: nucleic acid
        ( C ) STRANDEDNESS: double- stranded
        ( D ) TOPOLOGY: linear ( x i ) SEQUENCE DESCRIPTION: SEQ ID NO: 1:

| | | | | | |
|---|---|---|---|---|---|
| CGCGAAGATG | CCCCGGCGCA | GCCTGCACGC | GGCGGCCGTG | CTCCTGCTGG | 50 |
| TGATCTTAAA | GGAACAGCCT | TCCAGCCCGG | CCCCAGTGAA | CGGTTCCAAG | 100 |
| TGGACTTATT | TTGGTCCTGA | TGGGGAGAAT | AGCTGGTCCA | AGAAGTACCC | 150 |
| GTCGTGTGGG | GGCCTGCTGC | AGTCCCCCAT | AGACCTGCAC | AGTGACATCC | 200 |
| TCCAGTATGA | CGCCAGCCTC | ACGCCCCTCG | AGTTCCAAGG | CTACAATCTG | 250 |
| TCTGCCAACA | AGCAGTTTCT | CCTGACCAAC | AATGGCCATT | CAGTGAAGCT | 300 |
| GAACCTGCCC | TCGGACATGC | ACATCCAGGG | CCTCCAGTCT | CGCTACAGTG | 350 |
| CCACGCAGCT | GCACCTGCAC | TGGGGGAACC | CGAATGACCC | GCACGGCTCT | 400 |
| GAGCATACCG | TCAGCGGACA | GCACTTCTCC | GCCGAGCTGC | ACATTGTCCA | 450 |
| TTATAACTCA | GACCTTTATC | CTGACGACAG | NACTGCCAGC | AACAAGTCAG | 500 |
| AAGACCTCGC | TGTCCTGGGT | GCTCTCATTG | AGATGGGCTC | CTTCAATCCG | 550 |

```
TCCTATGACA   AGATCTTCAG   TCACCTTCAA   CATGTAAAGT   ACAAAGGCCA          600

GGAAGCATTC   GTCCCGGGAT   TCAACATTGA   AGAGCTGCTT   CCGGAGAGGA          650

CCGCTGAATA   TTACCGCTAC   CGGGGGTCCC   TGATCACACC   CCCTTGCAAC          700

CCCACTGTGC   TCTGGACAGT   TTTCCGAAAC   CCCGTGCAAA   TTTCCCAGGA          750

GCAGCTGCTG   GCTTTGGAGA   CAGCCCTGTA   CTGCACACAC   ATGGACGACC          800

CTTCCCCCAG   AGAAATGATC   AACAACTTCC   GGCAGGTCCA   GAAGTTCGAT          850

GAGAGGCTGG   TATACACCTC   CTTCTCCCAA   GTGCAAGTCT   GTACTGCGGC          900

AGGACTGAGT   CTGGGCATCA   TCCTCTCACT   GGCCCTGGCT   GGCATTCTTG          950

GCATCTGTAT   TGTGGTGGTG   GTGTCCATTT   GGCTTTTCAG   AAGGAAGAGT         1000

ATCAAAAAAG   GTGATAACAA   GGGAGTCATT   TACAAGCCAG   CCACCAAGAT         1050

GGAGACTGAG   GCCCACGCTT   GAGGTCCCCG   GAGCTCCCGG   GCACATCCAG         1100

GAAGGACCTT   GCTTTGGACC   CTACACACTT   CGGCTCTCTG   GACACTTGCG         1150

ACACCTCAAG   GTGTTCTCTG   TAGCTCAATC   TGCAAACATG   CCAGGCCTCA         1200

GGGATCCTCT   GCTGGGTGCC   TCCTTGTCTT   GGGACCATGG   NCACCCAGA          1250

GCCATCCGAT   CGATGGATGG   GATGCACTCT   CAGACCAAGC   AGCAGGAATT         1300

CAAAGCTGCT   TGCTGTAATT   GTGTGAGATT   GTGAAGTGGT   CTGAATTCTG         1350

GAATCACAAA   CCAACCATGC   TGGTGGGCCA   TTAATGGTTG   GAAAACACTT         1400

CCATCCGGGG   CTTTGCCAGA   GCGTGCTTTC   AAGTGTCCTG   GAAATTCTGC         1450

TGCTTCTCCA   AGCTTTCAGA   CAAGAATGTG   CACTCTCTGC   TTAGGTTTTG         1500

CTTGGGAAAC   TCAACTTCTT   TCCTCTGGAG   ACGGGACATC   TCCCTCTGAT         1550

TTCCTTCTGC   TATGCAAAAC   CTTTAATCTG   CACCTTACAN   ACTCGGGGAC         1600

AAATGGGGAC   AGGAAGGATC   AAGTTGTAGA   GNAGAAAAAG   AAAACAAGAG         1650

ATATACATTG   TGATATATAT   TAGGGACACT   TTCACAGTCC   TGTCCTCTGG         1700

ATCACAGACA   CTGCACAGAC   CTTAGGGAAA   TGGCAGGTTC   AAAGTTCCAC         1750

TTCTTGGTGG   GGATGAGAAG   GGAGAGAGAG   CTAGAGGGAC   AAAGAGAATG         1800

AGAAGACATG   GATGATCTGG   GAGAGTCTCA   CTTCGGAATC   AGAATTGGAA         1850

TCACATTCTG   TTTATCAAGC   CATAATGTAA   GGACAGAATA   ATACAATAAT         1900

AAGTCCAAAT   CCAACCTCCT   GTCAGTGGAA   CAGTTATGTT   TTATACTCTA         1950

CAGATTTTAC   AAATANATGA   GGCTNGTTCC   TTGAAAANTG   TGTTGNNTTG         2000

CTGTNGTCCN   NTGGAGGAGA   CATGAGTTCC   GAGATGACCA   ACTCNNGCNT         2050

TGNATNCTNG   GAGGNAATAN   GGCAGAACCA   AAATGACTGT   AGAACTTATT         2100

CTCTGTAGGC   CAAATTTCAT   TTCAGCCACT   TCTGCAGGAT   CCTACTGCCA         2150

ACCTGGAATG   GAGACTTTTA   TCTACTTCTC   TCTCTCTGAA   GATGTCAAAT         2200

CGTGGTTTAG   ATCAAATATA   TTTCAAGCTA   TAAAAGCAGG   AGGTTATCTG         2250

TGCAGGGGGC   TGGCATCATG   TATTTAGGGG   CAAGTAATAA   TGGAATGCTA         2300

CTAAGATACT   CCATATTCTT   CCCCGAATCA   CACAGACAGT   TTCTGACAGG         2350

CGCAACTCCT   CCATTTTCCT   CCCGCAGGTG   AGAACCCTGT   GGAGATGAGT         2400

CAGTGCCATG   ACTGAGAAGG   AACCGACCCC   TAGTTGAGAG   CACCTTGCAG         2450

TTCCCCGAGA   ACTTTCTGAT   TGCACAGTCT   CATTTTGACA   GCATGAAATG         2500

TCCTCTTGAA   GCATAGCTTT   TTAAATATCT   TTTTCCTTCT   ACTCCTCCCT         2550
```

-continued

| | | | | | |
|---|---|---|---|---|---|
| CTGACTCTAG | GAATTCTCTC | TTCTGGAATC | GCTTGAACCC | AGGAGGCGGA | 2600 |
| GGTTGCAGTA | AGCCAAGGTC | ATGCCACTGC | ACTCTAGCCT | GGGTGACAGA | 2650 |
| GCGAGACTCC | ATCTCAAAAA | AAAAAAAA | | | 2679 |

(2) INFORMATION FOR SEQ ID NO: 2:

(i) SEQUENCE CHARACTERISTICS:
        (A) LENGTH: 931 base pairs
        (B) TYPE: nucleic acid
        (C) STRANDEDNESS: double-stranded
        (D) TOPOLOGY: linear (xi) SEQUENCE DESCRIPTION: SEQ ID NO: 2:

| | | | | | |
|---|---|---|---|---|---|
| ACTTTCTCTC | TCTTTCGATT | CTTCCATACT | CAGAGTACGC | ACGGTCTGAT | 50 |
| TTTCTCTTTG | GATTCTTCCA | AAATCAGAGT | CAGACTGCTC | CCGGTGCCAT | 100 |
| GAACGGAGAC | GACGCCTTTG | CAAGGAGACC | CACGGTTGGT | GCTCAAATAC | 150 |
| CAGAGAAGAT | CCAAAAGGCC | TTCGATGATA | TTGCCAAATA | CTTCTCTAAG | 200 |
| GAAGAGTGGG | AAAAGATGAA | AGCCTCGGAG | AAAATCTTCT | ATGTGTATAT | 250 |
| GAAGAGAAAG | TATGAGGCTA | TGACTAAACT | AGGTTTCAAG | GCCACCCTCC | 300 |
| CACCTTTCAT | GTGTAATAAA | CGGGCCGAAG | ACTTCCAGGG | GAATGATTTG | 350 |
| GATAATGACC | CTAACCGTGG | GAATCAGGTT | GAACGTCCTC | AGATGACTTT | 400 |
| CGGCAGGCTC | CAGGGAATCT | CCCCGAAGAT | CATGCCCAAG | AAGCCAGCAG | 450 |
| AGGAAGGAAA | TGATTCGGAG | GAAGTGCCAG | AAGCATCTGG | CCCACAAAAT | 500 |
| GATGGGAAAG | AGCTGTGCCC | CCCGGGAAAA | CCAACTACCT | CTGAGAAGAT | 550 |
| TCACGAGAGA | TCTGGACCCA | AAGGGGGGA | ACATGCCTGG | ACCCACAGAC | 600 |
| TGCGTGAGAG | AAAACAGCTG | GTGATTTATG | AAGAGATCAG | CGACCCTGAG | 650 |
| GAAGATGACG | AGTAACTCCC | CTCAGGGATA | CGACACATGC | CCATGATGAG | 700 |
| AAGCAGAACG | TGGTGACCTT | TCACGAACAT | GGGCATGGCT | GCGGACCCCT | 750 |
| CGTCATCAGG | TGCATAGCAA | GTGAAAGCAA | GTGTTCACAA | CAGTGAAAAG | 800 |
| TTGAGCGTCA | TTTTCTTAG | TGTGCCAAGA | GTTCGATGTT | AGCGTTACG | 850 |
| TTGTATTTTC | TTACACTGTG | TCATTCTGTT | AGATACTAAC | ATTTCATTGA | 900 |
| TGACGAAGAC | ATACTTAATC | GATATTTGGT | T | | 931 |

(2) INFORMATION FOR SEQ ID NO: 3:

(i) SEQUENCE CHARACTERISTICS:
        (A) LENGTH: 1692 base pairs
        (B) TYPE: nucleic acid
        (C) STRANDEDNESS: double-stranded
        (D) TOPOLOGY: linear (xi) SEQUENCE DESCRIPTION: SEQ ID NO: 3:

| | | | | | |
|---|---|---|---|---|---|
| GATCCCCCGG | GCTGCAGGAA | TTCGGCACGA | GCAAAGGACT | TCCTAGTGGG | 50 |
| TGTGAAAGGC | AGCGGTGGCC | ACAGAGGCGG | CGGAGAGATG | GCCTTCAGCG | 100 |
| GTTCCCAGGC | TCCCTACCTG | AGTCCAGCTG | TCCCCTTTTC | TGGGACTATT | 150 |
| CAAGGAGGTC | TCCAGGACGG | ACTTCAGATC | ACTGTCAATG | GGACCGTTCT | 200 |
| CAGCTCCAGT | GGAACCAGGT | TTGCTGTGAA | CTTTCAGACT | GGCTTCAGTG | 250 |
| GAAATGACAT | TGCCTTCCAC | TTCAACCCTC | GGTTTGAAGA | TGGAGGGTAC | 300 |
| TTGGTGTCCA | ACACGAGGCA | GAACGGAAGC | TGGGGCCCG | AGGAGAGGAA | 350 |

|  |  |  |  |  |
|---|---|---|---|---|
| GACACACATG | CCTTNCCAGA | AGGGGATGCC | CTTTGACCTC | TGCTTCCTGG | 400 |
| TGCAGAGCTC | AGATTTCAAG | GTGATGGTGA | ACGGGATCCT | CTTCGTGCAG | 450 |
| TACTTCACAT | CTCGTCATGC | CCTGTCCACC | GTTGTGGACA | CCATCTCCGT | 500 |
| CAATGGCTCT | GTGCAGCTGT | CCTACATCAG | CTTCCAGCCT | CCCGGCGTGT | 550 |
| GGCCTGCCAA | CCCGGCTCCC | ATTACCCAGA | CAGNNNTCAT | CCACACAGTN | 600 |
| GCAGAGCGCC | CNCTGGACAG | ATGTCTCTAC | TCCCGCCATC | CCACCTATGA | 650 |
| TGTACCCCCA | CCCCGCCTAT | CCGATGCCTT | TCATCACCAC | CATTCTGGGA | 700 |
| GGGCTGTACC | CATCCAAGTC | CATCCTCCTG | TCAGGCACTG | TNCTGCCCAG | 750 |
| TGCTCANGAG | GTTCCACATC | NAACCTGTGC | NCTGGGAACC | ACATCGCCTT | 800 |
| CCACCTGAAC | CCCCGTTTTG | ATGAGAATGC | TGTGGTCCGC | AACACCCAGA | 850 |
| TCGACAACTC | CTGGGGGTCT | CAGGAGCGAA | GTCTGCCCCG | AAAAATGCCC | 900 |
| TTCGTCCGTG | GCCAGAGCTT | CTCAGTGTGG | ATCTTGTGTG | AAGCTCACTG | 950 |
| CCTCAAGGTG | GCCGTGGATG | GTCAGCACCT | GTTTGAATAC | AACCATCGCC | 1000 |
| TGAGGAACCT | GCCCACCATC | AACAGACTGG | AAGTGGGGGG | CGACATCCAG | 1050 |
| CTGACCATGT | GCAGACATAG | GCGGCTTCCT | GGCCCTGGGG | CCGGGGCTG | 1100 |
| GGGTGTGGGG | CAGTCTGGGT | CCTCTCATCA | TCCCCACTTC | CCAGGCCCAG | 1150 |
| CCTTTCCAAC | CCTGCCTGGG | ATCTGGGCTT | TAATGCAGAG | GCCATGTCCT | 1200 |
| TGTCTGGTCC | TGCTTCTGGC | TACAGCCACC | CTGGAACGGA | GAAGGCAGCT | 1250 |
| GACGGGGATT | GCCTCCTCAG | CCGCAGCAGC | ACCTGGGGCT | CCAGCTGCTG | 1300 |
| GAATCCTACC | ATCCCAGGAY | GCAGGCACAG | CCAGGGAGAG | GGGAGGNGTG | 1350 |
| GGCAGTGAAG | ATGAAGCCCC | ATGCTCAGTC | CCCTCCCATC | CCCCACGCAG | 1400 |
| CTCCACCCCA | GTCCCAAGCC | ACCAGCTGTC | TGCTCCTGGT | GGGAGGTGGC | 1450 |
| CTCCTCAGCN | CCTCCTCTCT | GACCTTTAAC | CTNACTCTCA | CCTTGCACCG | 1500 |
| TGCACCAACC | CTTCACCCCT | CCTGGAAAGC | AGGCCTGATG | GCTTCCCACT | 1550 |
| GGCCTCCACC | ACCTGACCAG | AGTGTTCTCT | TCAGAGGACT | GGCTCCTTTC | 1600 |
| CCAGTGTCCT | TAAAATAAAG | AAATGAAAAT | NCTTGTTGGC | AAAAAAAAA | 1650 |
| AAAAAAAAAC | TCGAGGGGCN | NCCCNGTACC | CAATTCGCCC | TA | 1692 |

( 2 ) INFORMATION FOR SEQ ID NO: 4:

( i ) SEQUENCE CHARACTERISTICS:
        ( A ) LENGTH: 1190 base pairs
        ( B ) TYPE: nucleic acid
        ( C ) STRANDEDNESS: double- stranded
        ( D ) TOPOLOGY: linear ( x i ) SEQUENCE DESCRIPTION: SEQ ID NO: 4:

|  |  |  |  |  |
|---|---|---|---|---|
| ATCTGCAGAA | TTCGGCTTCG | ATCTAGAACT | AGTGGATCCC | CCGGGCTGCA | 50 |
| GGAATTCGGC | ACGAGCGGTT | CCAAGTGGAC | TTATTTTGGT | CCTGATGGGG | 100 |
| AGAATAGCTG | GTCCAAGAAG | TACCCGTCGT | GTGGGGGCCT | GCTGCAGTCC | 150 |
| CCCATAGACC | TGCACAGTGA | CATCCTCCAG | TATGACGCCA | GCCTCACGCC | 200 |
| CCTCGAGTTC | CAAGGCTACA | ATCTGTCTGC | CAACAAGCAG | TTTCTCCTGA | 250 |
| CCAACAATGG | CCATTCAGTG | AAGCTGAACC | TGCCCTCGGA | CATGCACATC | 300 |
| CAGGGCCTCC | AGTCTCGCTA | CAGTGCCACG | CAGCTGCACC | TGCACTGGGG | 350 |

-continued

| | | | | |
|---|---|---|---|---|
| GAACCCGAAT | GACCCGCACG | GCTCTGAGCA | TACCGTCAGC | GGACAGCACT | 400 |
| TCTCCGCCGA | GCTGCACATT | GTCCATTATA | ACTCAGACCT | TTATCCTGAC | 450 |
| GACAGNACTG | CCAGCAACAA | GTCAGAAGAC | CTCGCTGTCC | TGGGTGCTCT | 500 |
| CATTGAGATG | GGCTCCTTCA | ATCCGTCCTA | TGACAAGATC | TTCAGTCACC | 550 |
| TTCAACATGT | AAAGTACAAA | GGCCAGGAAG | CATTCGTCCC | GGGATTCAAC | 600 |
| ATTGAAGAGC | TGCTTCCGGA | GAGGACCGCT | GAATATTACC | GCTACCGGGG | 650 |
| GTCCCTGATC | ACACCCCTT | GCAACCCAC | TGTGCTCTGG | ACAGTTTTCC | 700 |
| GAAACCCCGT | GCAAATTTCC | CAGGAGCAGC | TGCTGGCTTT | GGAGACAGCC | 750 |
| CTGTACTGCA | CACACATGGA | CGACCCTTCC | CCCAGAGAAA | TGATCAACAA | 800 |
| CTNCCGGCAG | GTCCAGAAGT | TCGNTGAGAG | GCTGGTATAC | ACCTCCTTCT | 850 |
| CNCAAGTGCA | AGTCTGTACT | GCGGCAGGAC | TGAGTCTGGG | CATCATCCTC | 900 |
| TCACTGGCCC | TGGCTGGCAT | TCTTGGCATC | TGTATTGTGG | TGGTGGTGTC | 950 |
| CATTTGGCTT | TTCAGAAGGA | AGAGTANCCC | CNAAAGGTGA | TAACAAGGGA | 1000 |
| GTCATTTACA | AGCCANCCAC | CAAGATGGAG | ACTGAGGCCC | ACGCTTGAGG | 1050 |
| TCCCCGGAGC | TCCCGGGCAC | ATCCAGGAAG | GACCTTGCTT | TTGGACCCTA | 1100 |
| CACACTTCGG | CTCTCTGGAC | ACTTGCGACA | CCTCAAGGTG | TTCTCTGTAG | 1150 |
| CTCAATCTGC | AAACATGCCA | GGCCTCAGGG | ATCCTCTGCT | | 1190 |

( 2 ) INFORMATION FOR SEQ ID NO: 5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

GCCAAATACT TCTCTAAGGA AGAGTGG                                                27

( 2 ) INFORMATION FOR SEQ ID NO: 6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

TTCACTGTTG TGAACACTTG CTTTCAC                                                27

( 2 ) INFORMATION FOR SEQ ID NO: 7:

( i ) SEQUENCE CHARACTERISTICS:
        ( A ) LENGTH: 2085 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 7:

```
G GAG CTC CAC CGC GGT GGC GGC CGC TCT AGA ACT AGT GGA TCC CCC        46
  Glu Leu His Arg Gly Gly Gly Arg Ser Arg Thr Ser Gly Ser Pro
                5                  10                  15

GGG CTG CAG GAA TTC GGC ACG AGC TGC TGC TCA CAG AGG AGG CCC AGT      94
Gly Leu Gln Glu Phe Gly Thr Ser Cys Cys Ser Gln Arg Arg Pro Ser
             20                  25                  30

CGG ACA GGA CTA TTG ACT GAA ACC TCC CGT TAC GCC AGG AAG ATC TCC     142
```

|     |     |     |     |     |     |     |     |     |     |     |     |     |     |     |     |
|-----|-----|-----|-----|-----|-----|-----|-----|-----|-----|-----|-----|-----|-----|-----|-----|
| Arg | Thr | Gly | Leu | Leu | Thr | Glu | Thr | Ser | Arg | Tyr | Ala | Arg | Lys | Ile | Ser |
|     |     |     |     | 35  |     |     |     |     | 40  |     |     |     | 45  |     |     |

| GGT | ACC | ACT | GCC | CTC | CAG | GAG | GCC | CTG | AAG | GAG | AAG | CAG | CAG | CAC | ATT | 190 |
|-----|-----|-----|-----|-----|-----|-----|-----|-----|-----|-----|-----|-----|-----|-----|-----|-----|
| Gly | Thr | Thr | Ala | Leu | Gln | Glu | Ala | Leu | Lys | Glu | Lys | Gln | Gln | His | Ile |     |
|     |     |     | 50  |     |     |     |     | 55  |     |     |     | 60  |     |     |     |     |

| GAG | CAG | CTG | CTG | GCG | GAA | CGG | GAT | CTG | GAG | AGG | GCG | GAG | GTG | GCC | AAG | 238 |
| Glu | Gln | Leu | Leu | Ala | Glu | Arg | Asp | Leu | Glu | Arg | Ala | Glu | Val | Ala | Lys |     |
|     | 65  |     |     |     |     | 70  |     |     |     |     | 75  |     |     |     |     |     |

| GCC | ACG | AGC | CAC | GTG | GGG | GAG | ATA | GAG | CAG | GAG | CTA | GCT | CTG | GCC | CGG | 286 |
| Ala | Thr | Ser | His | Val | Gly | Glu | Ile | Glu | Gln | Glu | Leu | Ala | Leu | Ala | Arg |     |
| 80  |     |     |     |     | 85  |     |     |     |     | 90  |     |     |     |     | 95  |     |

| GAC | GGA | CAT | GAC | CAG | CAT | GTC | CTG | GAA | TTG | GAA | GCC | AAA | ATG | GAC | CAG | 334 |
| Asp | Gly | His | Asp | Gln | His | Val | Leu | Glu | Leu | Glu | Ala | Lys | Met | Asp | Gln |     |
|     |     |     |     | 100 |     |     |     |     | 105 |     |     |     |     | 110 |     |     |

| CTG | CGA | ACA | ATG | GTG | GAA | GCT | GCT | GAC | AGG | GAG | AAG | GTG | GAG | CTT | CTC | 382 |
| Leu | Arg | Thr | Met | Val | Glu | Ala | Ala | Asp | Arg | Glu | Lys | Val | Glu | Leu | Leu |     |
|     |     |     | 115 |     |     |     |     | 120 |     |     |     |     | 125 |     |     |     |

| AAC | CAG | CTT | GAA | GAG | GAG | AAA | AGG | AAG | GTT | GAG | GAC | CTT | CAG | TTC | CGG | 430 |
| Asn | Gln | Leu | Glu | Glu | Glu | Lys | Arg | Lys | Val | Glu | Asp | Leu | Gln | Phe | Arg |     |
|     |     | 130 |     |     |     |     | 135 |     |     |     |     | 140 |     |     |     |     |

| GTT | GAA | GAA | GAA | TCA | ATT | ACC | AAA | GGT | GAT | CTT | GAG | ACG | CAG | ACC | AAA | 478 |
| Val | Glu | Glu | Glu | Ser | Ile | Thr | Lys | Gly | Asp | Leu | Glu | Thr | Gln | Thr | Lys |     |
|     | 145 |     |     |     |     | 150 |     |     |     |     | 155 |     |     |     |     |     |

| CTG | GAG | CAT | GCC | CGC | ATT | AAG | GAG | CTT | GAA | CAG | AGC | CTG | CTC | TTT | GAA | 526 |
| Leu | Glu | His | Ala | Arg | Ile | Lys | Glu | Leu | Glu | Gln | Ser | Leu | Leu | Phe | Glu |     |
| 160 |     |     |     |     | 165 |     |     |     |     | 170 |     |     |     |     | 175 |     |

| AAG | ACC | AAA | GCT | GAC | AAA | CTC | CAG | AGG | GAG | TTA | GAA | GAC | ACT | AGG | GTG | 574 |
| Lys | Thr | Lys | Ala | Asp | Lys | Leu | Gln | Arg | Glu | Leu | Glu | Asp | Thr | Arg | Val |     |
|     |     |     |     | 180 |     |     |     |     | 185 |     |     |     |     | 190 |     |     |

| GCT | ACA | GTT | TCA | GAA | AAG | TCA | CGT | ATA | ATG | GAA | CTG | GAG | AAA | GAC | CTA | 622 |
| Ala | Thr | Val | Ser | Glu | Lys | Ser | Arg | Ile | Met | Glu | Leu | Glu | Lys | Asp | Leu |     |
|     |     |     | 195 |     |     |     |     | 200 |     |     |     |     | 205 |     |     |     |

| GCA | TTG | AGA | GTA | CAG | GAA | GTA | GCT | GAG | CTC | CGA | AGA | AGG | CTA | GAG | TCC | 670 |
| Ala | Leu | Arg | Val | Gln | Glu | Val | Ala | Glu | Leu | Arg | Arg | Arg | Leu | Glu | Ser |     |
|     |     | 210 |     |     |     |     | 215 |     |     |     |     | 220 |     |     |     |     |

| AAT | AAG | CCT | GCT | GGG | GAT | GTG | GAC | ATG | TCA | CTT | TCC | CTT | TTG | CAA | GAG | 718 |
| Asn | Lys | Pro | Ala | Gly | Asp | Val | Asp | Met | Ser | Leu | Ser | Leu | Leu | Gln | Glu |     |
|     | 225 |     |     |     |     | 230 |     |     |     |     | 235 |     |     |     |     |     |

| ATA | AGC | TCT | TTG | CAA | GAA | AAG | TTA | GAA | GTC | ACC | CGT | ACT | GAC | CAC | CAG | 766 |
| Ile | Ser | Ser | Leu | Gln | Glu | Lys | Leu | Glu | Val | Thr | Arg | Thr | Asp | His | Gln |     |
| 240 |     |     |     |     | 245 |     |     |     |     | 250 |     |     |     |     | 255 |     |

| AGA | GAA | ATA | ACT | TCT | CTG | AAG | GAG | CAT | TTT | GGA | GCC | CGG | GAA | GAA | ACT | 814 |
| Arg | Glu | Ile | Thr | Ser | Leu | Lys | Glu | His | Phe | Gly | Ala | Arg | Glu | Glu | Thr |     |
|     |     |     |     | 260 |     |     |     |     | 265 |     |     |     |     | 270 |     |     |

| CAT | CAG | AAG | GAG | ATA | AAG | GCT | CTG | TAT | ACC | GCC | ACG | GAA | AAG | CTT | TCC | 862 |
| His | Gln | Lys | Glu | Ile | Lys | Ala | Leu | Tyr | Thr | Ala | Thr | Glu | Lys | Leu | Ser |     |
|     |     |     | 275 |     |     |     |     | 280 |     |     |     |     | 285 |     |     |     |

| AAA | GAG | AAC | GAG | TCA | TTG | AAA | AGC | AAG | CTG | GAG | CAT | GCC | AAC | AAA | GAG | 910 |
| Lys | Glu | Asn | Glu | Ser | Leu | Lys | Ser | Lys | Leu | Glu | His | Ala | Asn | Lys | Glu |     |
|     |     | 290 |     |     |     |     | 295 |     |     |     |     | 300 |     |     |     |     |

| AAC | TCA | GAT | GTG | ATA | GCT | CTA | TGG | AAG | TCC | AAA | CTG | GAG | ACT | GCC | ATC | 958 |
| Asn | Ser | Asp | Val | Ile | Ala | Leu | Trp | Lys | Ser | Lys | Leu | Glu | Thr | Ala | Ile |     |
|     | 305 |     |     |     |     | 310 |     |     |     |     | 315 |     |     |     |     |     |

| GCA | TCC | CAC | CAG | CAG | GCG | ATG | GAA | GAA | CTG | AAG | GTA | TCT | TTC | AGC | AAA | 1006 |
| Ala | Ser | His | Gln | Gln | Ala | Met | Glu | Glu | Leu | Lys | Val | Ser | Phe | Ser | Lys |      |
| 320 |     |     |     |     | 325 |     |     |     |     | 330 |     |     |     |     | 335 |      |

| GGG | CTT | GGA | ACA | GAG | ACG | GCA | GAA | TTT | GCT | GAA | CTA | AAA | ACA | CAA | ATA | 1054 |
| Gly | Leu | Gly | Thr | Glu | Thr | Ala | Glu | Phe | Ala | Glu | Leu | Lys | Thr | Gln | Ile |      |
|     |     |     || 340 |     |     |     |     | 345 |     |     |     |     | 350 |     |      |

| GAG | AAA | ATG | AGA | CTA | GAT | TAC | CAA | CAC | GAA | ATA | GAA | AAT | TTG | CAG | AAT | 1102 |

```
          Glu Lys Met Arg Leu Asp Tyr Gln His Glu Ile Glu Asn Leu Gln Asn
                  355                 360                 365

CAA CAA GAC TCT GAA CGG GCT GCC CAT GCT AAA GAG ATG GAA GCC TTG               1150
Gln Gln Asp Ser Glu Arg Ala Ala His Ala Lys Glu Met Glu Ala Leu
        370                 375                 380

AGG GCT AAA CTG ATG AAA GTT ATT AAA GAA AAG GAA AAC AGT CTG GAA               1198
Arg Ala Lys Leu Met Lys Val Ile Lys Glu Lys Glu Asn Ser Leu Glu
385                 390                 395

GCC ATC AGG TCG AAA CTG GAC AAA GCA GAA GAC CAG CAT CTC GTA GAA               1246
Ala Ile Arg Ser Lys Leu Asp Lys Ala Glu Asp Gln His Leu Val Glu
400                 405                 410                 415

ATG GAA GAC ACG TTA AAC AAA TTA CAG GAA GCT GAA ATA AAG GTA AAG               1294
Met Glu Asp Thr Leu Asn Lys Leu Gln Glu Ala Glu Ile Lys Val Lys
                    420                 425                 430

GAG CTA GAG GTA CTG CAA GCC AAA TGC AAT GAA CAA ACC AAG GTT ATT               1342
Glu Leu Glu Val Leu Gln Ala Lys Cys Asn Glu Gln Thr Lys Val Ile
                435                 440                 445

GAT AAT TTT ACA TCA CAG CTC AAG GCT ACT GAA GAA AAG CTC TTG GAT               1390
Asp Asn Phe Thr Ser Gln Leu Lys Ala Thr Glu Glu Lys Leu Leu Asp
            450                 455                 460

CTT GAT GCA CTT CGG AAA GCC AGT TCC GAA GGT AAA TCG GAA ATG AAG               1438
Leu Asp Ala Leu Arg Lys Ala Ser Ser Glu Gly Lys Ser Glu Met Lys
        465                 470                 475

AAA CTT AGA CAG CAG CTT GAG GCA GCT GAG AAA CAG ATT AAA CAT TTA               1486
Lys Leu Arg Gln Gln Leu Glu Ala Ala Glu Lys Gln Ile Lys His Leu
480                 485                 490                 495

GAG ATT GAA AAG AAT GCT GAA AGT AGC AAG GCT AGT AGC ATT ACC AGA               1534
Glu Ile Glu Lys Asn Ala Glu Ser Ser Lys Ala Ser Ser Ile Thr Arg
                    500                 505                 510

GAG CTC CAG GGG AGA GAG CTA AAG CTT ACT AAC CTT CAG GAA AAT TTG               1582
Glu Leu Gln Gly Arg Glu Leu Lys Leu Thr Asn Leu Gln Glu Asn Leu
                515                 520                 525

AGT GAA GTC AGT CAA GTG AAA GAG ACT TTG GAA AAA GAA CTT CAG ATT               1630
Ser Glu Val Ser Gln Val Lys Glu Thr Leu Glu Lys Glu Leu Gln Ile
            530                 535                 540

TTG AAA GAA AAG TTT GCT GAA GCT TCA GAG GAG GCA GTC TCT GTT CAG               1678
Leu Lys Glu Lys Phe Ala Glu Ala Ser Glu Glu Ala Val Ser Val Gln
        545                 550                 560

AGA AGT ATG CAA GAA ACT GTA AAT AAG TTA CAC CAA AAG GAG GAA CAG               1726
Arg Ser Met Gln Glu Thr Val Asn Lys Leu His Gln Lys Glu Glu Gln
565                 570                 575                 580

TTT AAC ATG CTG TCT TCT GAC TTG GAG AAG CTG AGA GAA AAC TTA GCA               1774
Phe Asn Met Leu Ser Ser Asp Leu Glu Lys Leu Arg Glu Asn Leu Ala
                    585                 590                 595

GAT ATG GAG GCA AAA TTT AGA GAG AAA GAT GAG AGA GAA GAG CAG CTG               1822
Asp Met Glu Ala Lys Phe Arg Glu Lys Asp Glu Arg Glu Glu Gln Leu
                600                 605                 610

ATA AAG GCA AAG GAA AAA CTG GAA AAT GAC ATT GCA GAA ATA ATG AAG               1870
Ile Lys Ala Lys Glu Lys Leu Glu Asn Asp Ile Ala Glu Ile Met Lys
            615                 620                 625

ATG TCA GGA GAT AAC TCT TCT CAG CTG ACA AAA ATG AAC GAT GAA TTA               1918
Met Ser Gly Asp Asn Ser Ser Gln Leu Thr Lys Met Asn Asp Glu Leu
        630                 635                 640

CGT CTG AAA GAA AGA GAT GTA GAA GAA TTA CAG CTA AAA CTT ACA AAG               1966
Arg Leu Lys Glu Arg Asp Val Glu Glu Leu Gln Leu Lys Leu Thr Lys
645                 650                 655                 660

GCT AAT GAA AAT GCA AGT TTT CTG CAA AAA AGT ATT GAG GAC ATG ACT               2014
Ala Asn Glu Asn Ala Ser Phe Leu Gln Lys Ser Ile Glu Asp Met Thr
                    665                 670                 675

GTC AAA GCT GAA CAG AGC CAG CAA GAA GCA GCT AAA AAG CAT GGA AAT               2062
```

```
Val Lys Ala Glu Gln Ser Gln Gln Glu Ala Ala Lys Lys His Gly Asn
            680                 685                 690

TAAGCACCCA CCACTGCCCT GGG                                                        2085
```

( 2 ) INFORMATION FOR SEQ ID NO: 8:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO: 8:

```
Xaa Leu Xaa Xaa Xaa Xaa Xaa Xaa Xaa
              5
```

( 2 ) INFORMATION FOR SEQ ID NO: 9:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO: 9:

```
Arg Leu Gln Gly Ile Ser Pro Lys Ile
              5
```

( 2 ) INFORMATION FOR SEQ ID NO: 10:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO: 10:

```
Arg Leu Arg Glu Arg Lys Gln Leu Val
              5
```

( 2 ) INFORMATION FOR SEQ ID NO: 11:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO: 11:

```
Lys Ile Gln Lys Ala Phe Asp Asp Ile
              5
```

( 2 ) INFORMATION FOR SEQ ID NO: 12:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO: 12:

```
Cys Leu Gly Gly Leu Leu Thr Met Val
              5
```

( 2 ) INFORMATION FOR SEQ ID NO: 13:

( i ) SEQUENCE CHARACTERISTICS:
        ( A ) LENGTH: 8 amino acids
        ( B ) TYPE: amino acid
        ( D ) TOPOLOGY: linear ( x i ) SEQUENCE DESCRIPTION: SEQ ID NO: 13:

```
Ile  Leu  Lys  Glu  Pro  Val  Gly  Val
                  5
```

( 2 ) INFORMATION FOR SEQ ID NO: 14:

( i ) SEQUENCE CHARACTERISTICS:
        ( A ) LENGTH: 9 amino acids
        ( B ) TYPE: amino acid
        ( D ) TOPOLOGY: linear ( i x ) FEATURE: The sixth amino acid is Ser, Lys or Phe. The ninth
                amino acid is Val or Ile ( x i ) SEQUENCE DESCRIPTION: SEQ ID NO: 14:

```
Xaa  Leu  Xaa  Xaa  Xaa  Xaa  Xaa  Xaa  Xaa
                    5
```